United States Patent [19]
Ross, Jr. et al.

[11] Patent Number: 5,968,043
[45] Date of Patent: Oct. 19, 1999

[54] PLASTIC DOUBLE NUT MECHANISM ENABLING RIGID ORTHOPEDIC DISTRACTION

[75] Inventors: John D. Ross, Jr., Ovilla; Mikhail L. Samchukov, Coppell; John G. Birch, Dallas, all of Tex.

[73] Assignee: Texas Scottish Rite Hospital for Children, Dallas, Tex.

[21] Appl. No.: 09/021,288

[22] Filed: Feb. 10, 1998

Related U.S. Application Data

[60] Continuation of application No. 08/448,922, May 25, 1995, which is a division of application No. 08/075,179, Jun. 10, 1993.

[51] Int. Cl.$^6$ .................................................. A61B 17/66
[52] U.S. Cl. ................... 606/56; 606/57; 606/54
[58] Field of Search ................... 606/54, 55, 56, 606/57, 58, 59

[56] References Cited

U.S. PATENT DOCUMENTS

| | | |
|---|---|---|
| 1,869,726 | 8/1932 | Youngren . |
| 1,997,466 | 4/1935 | Longfellow . |
| 2,035,952 | 3/1936 | Ettinger . |
| 2,055,024 | 9/1936 | Bittner, Jr. . |
| 2,056,749 | 10/1936 | Thomas . |
| 2,101,889 | 12/1937 | Anderson . |
| 2,120,446 | 6/1938 | Thomas . |
| 2,198,871 | 4/1940 | Haboush . |
| 2,214,490 | 9/1940 | Thomas . |
| 2,238,870 | 4/1941 | Haynes . |
| 2,250,417 | 7/1941 | Ettinger . |
| 2,346,346 | 4/1944 | Anderson . |
| 2,391,537 | 12/1945 | Anderson . |
| 2,406,987 | 9/1946 | Anderson . |
| 2,439,995 | 4/1948 | Thrailkill . |
| 2,497,626 | 2/1950 | Persall . |
| 2,687,720 | 8/1954 | Haboush . |
| 3,727,610 | 4/1973 | Riniker . |

(List continued on next page.)

FOREIGN PATENT DOCUMENTS

| | | |
|---|---|---|
| 0188954 | 7/1986 | European Pat. Off. . |
| 0369017 | 11/1989 | European Pat. Off. . |
| 723841 | 4/1932 | France . |
| 775126 | 12/1934 | France . |
| 367858 | 4/1973 | Russian Federation . |
| 586907 | 1/1978 | Russian Federation . |
| 611612 | 5/1978 | Russian Federation . |
| 534045 | 7/1979 | Russian Federation . |
| 827049 | 5/1981 | Russian Federation . |
| 984468 | 12/1982 | Russian Federation . |
| 1022702 | 6/1983 | Russian Federation . |
| 1050678 | 10/1983 | Russian Federation . |
| 1127578 | 12/1984 | Russian Federation . |
| 1725865 | 4/1992 | Russian Federation . |
| 667205 | 6/1979 | U.S.S.R. . |
| 735248 | 6/1980 | U.S.S.R. . |

(List continued on next page.)

*Primary Examiner*—Michael Buiz
*Assistant Examiner*—David O. Reip
*Attorney, Agent, or Firm*—Fulbright & Jaworski L.L.P.

[57] ABSTRACT

A distraction apparatus for an external fixation device used to rigidly immobilize bone fragments during bone lengthening and angular deformity correction includes distractor mechanisms and pivotable spacers for connecting frame members of an external fixator, and wire and half pin fasteners. The interconnected distractor mechanisms, pivotable spacers and frame members form a rigid structure with rigidity which is maintained during adjustment of the distraction. For linear distraction, the distraction mechanism is a single screw assembly with a single-threaded rod and dual plastic nuts disposed either side of a metallic adjustment surface. After tightening down, the nuts may be synchronously co-rotated, advantageously using a tool such as a double wrench engaging on aligned faces of the nuts. This synchronous co-rotation causes linear displacement along the threaded rod, thereby enabling distraction. Further, the metal-to-plastic inter-face between the nuts and the adjustment surface facilitates this synchronous co-rotating without causing loosening of the nuts, thereby minimizing the introduction of play in the mechanism during distraction.

15 Claims, 9 Drawing Sheets

U.S. PATENT DOCUMENTS

| | | |
|---|---|---|
| 3,941,123 | 3/1976 | Volkov et al. . |
| 3,976,061 | 8/1976 | Volkov et al. . |
| 3,977,397 | 8/1976 | Kalnberz et al. . |
| 3,985,127 | 10/1976 | Volkov et al. . |
| 3,993,055 | 11/1976 | Volkov et al. . |
| 4,006,740 | 2/1977 | Volkov et al. . |
| 4,033,340 | 7/1977 | Kalnberz . |
| 4,100,919 | 7/1978 | Oganesyan et al. . |
| 4,127,119 | 11/1978 | Kronner . |
| 4,185,623 | 1/1980 | Volkov et al. . |
| 4,256,112 | 3/1981 | Kopf et al. . |
| 4,271,832 | 6/1981 | Evans et al. . |
| 4,308,863 | 1/1982 | Fischer . |
| 4,312,336 | 1/1982 | Danieletto et al. . |
| 4,338,927 | 7/1982 | Volkov et al. . |
| 4,365,624 | 12/1982 | Jaquet . |
| 4,404,967 | 9/1983 | Bacal et al. . |
| 4,463,758 | 8/1984 | Patil et al. . |
| 4,502,473 | 3/1985 | Harris et al. . |
| 4,541,422 | 9/1985 | de Zbikowski . |
| 4,548,199 | 10/1985 | Agee . |
| 4,554,915 | 11/1985 | Brumfield . |
| 4,573,459 | 3/1986 | Litton . |
| 4,583,897 | 4/1986 | Briles . |
| 4,611,586 | 9/1986 | Agee et al. . |
| 4,615,338 | 10/1986 | Ilizarov et al. . |
| 4,628,919 | 12/1986 | Clyburn . |
| 4,658,809 | 4/1987 | Ulrich et al. . |
| 4,662,365 | 5/1987 | Gotzen et al. . |
| 4,730,608 | 3/1988 | Schlein . |
| 4,745,913 | 5/1988 | Castaman et al. . |
| 4,768,524 | 9/1988 | Hardy . |
| 4,784,125 | 11/1988 | Monticelli et al. . |
| 4,922,896 | 5/1990 | Agee et al. . |
| 4,931,055 | 6/1990 | Bumpus et al. . |
| 4,973,331 | 11/1990 | Pursley et al. . |
| 4,978,348 | 12/1990 | Ilizarov . |
| 4,988,349 | 1/1991 | Pennig . |
| 5,015,205 | 5/1991 | Franks, Jr. . |
| 5,129,388 | 7/1992 | Vignaud et al. . |

FOREIGN PATENT DOCUMENTS

| | | |
|---|---|---|
| 858797 | 8/1981 | U.S.S.R. . |
| 421788 | 1/1935 | United Kingdom . |
| 1481585 | 8/1977 | United Kingdom . |
| 2031731 | 4/1980 | United Kingdom . |
| 9111967 | 8/1991 | WIPO . |
| 9207526 | 5/1992 | WIPO . |

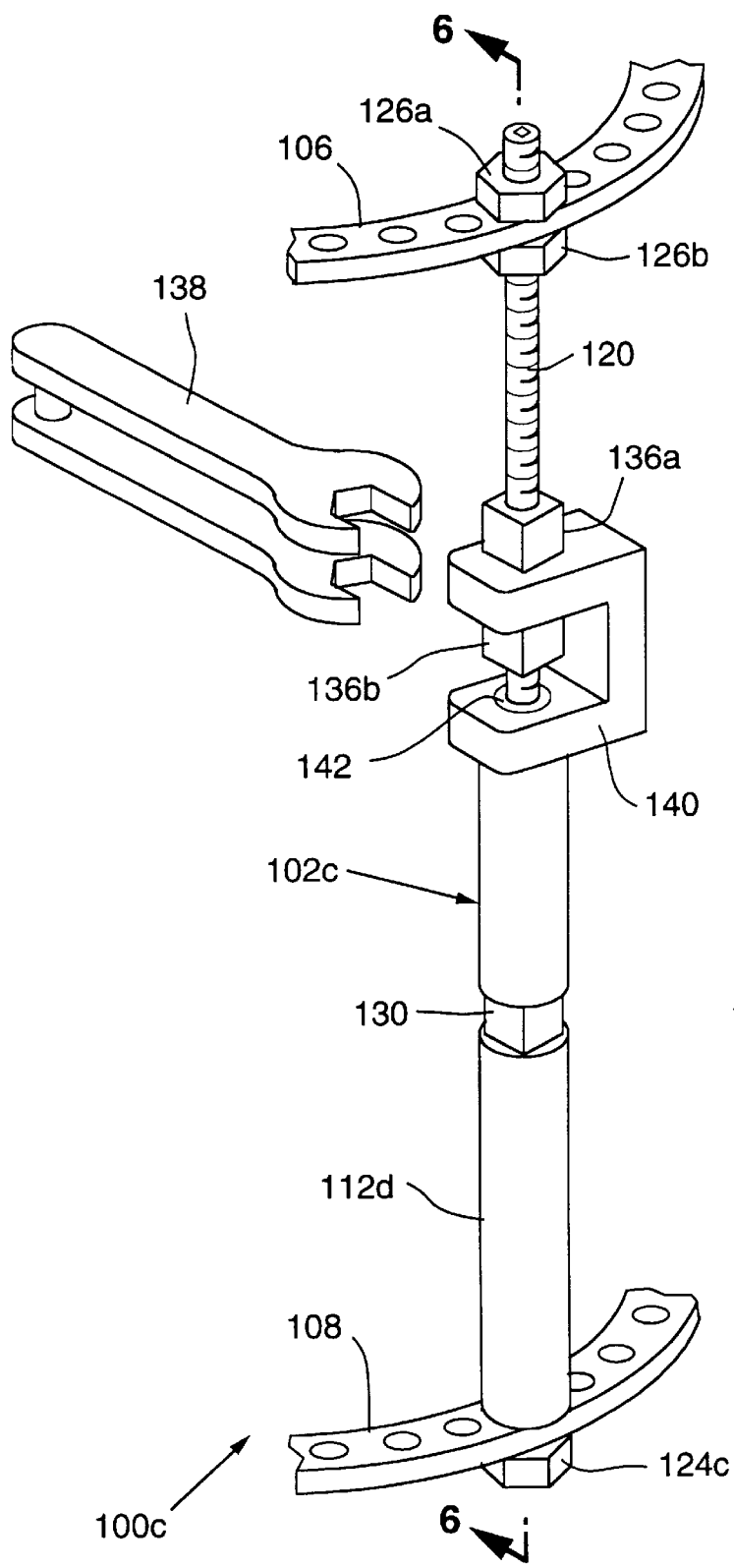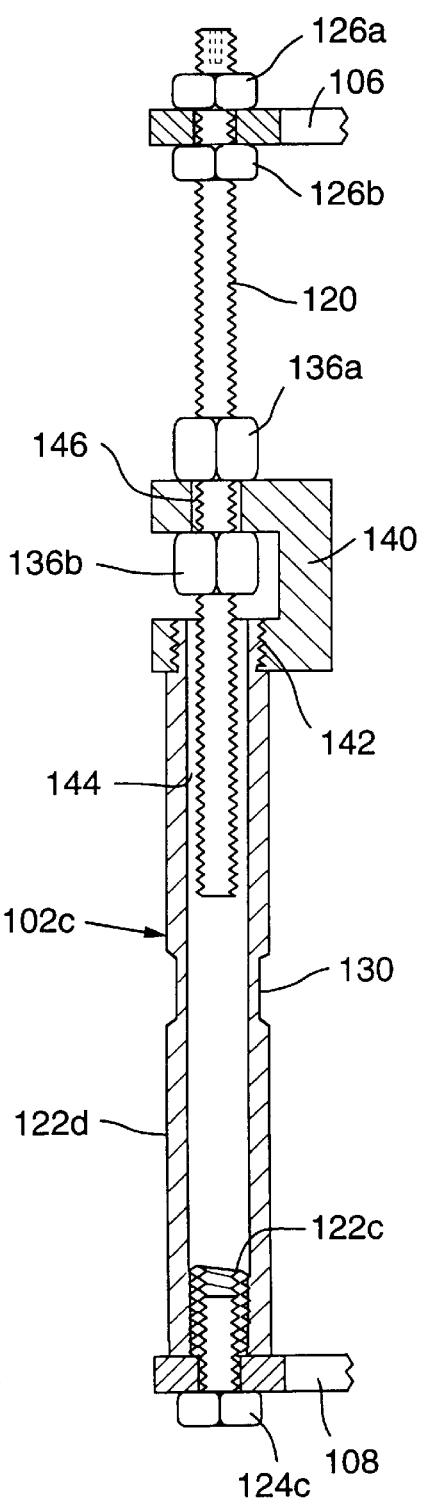
FIG. 5    FIG. 6

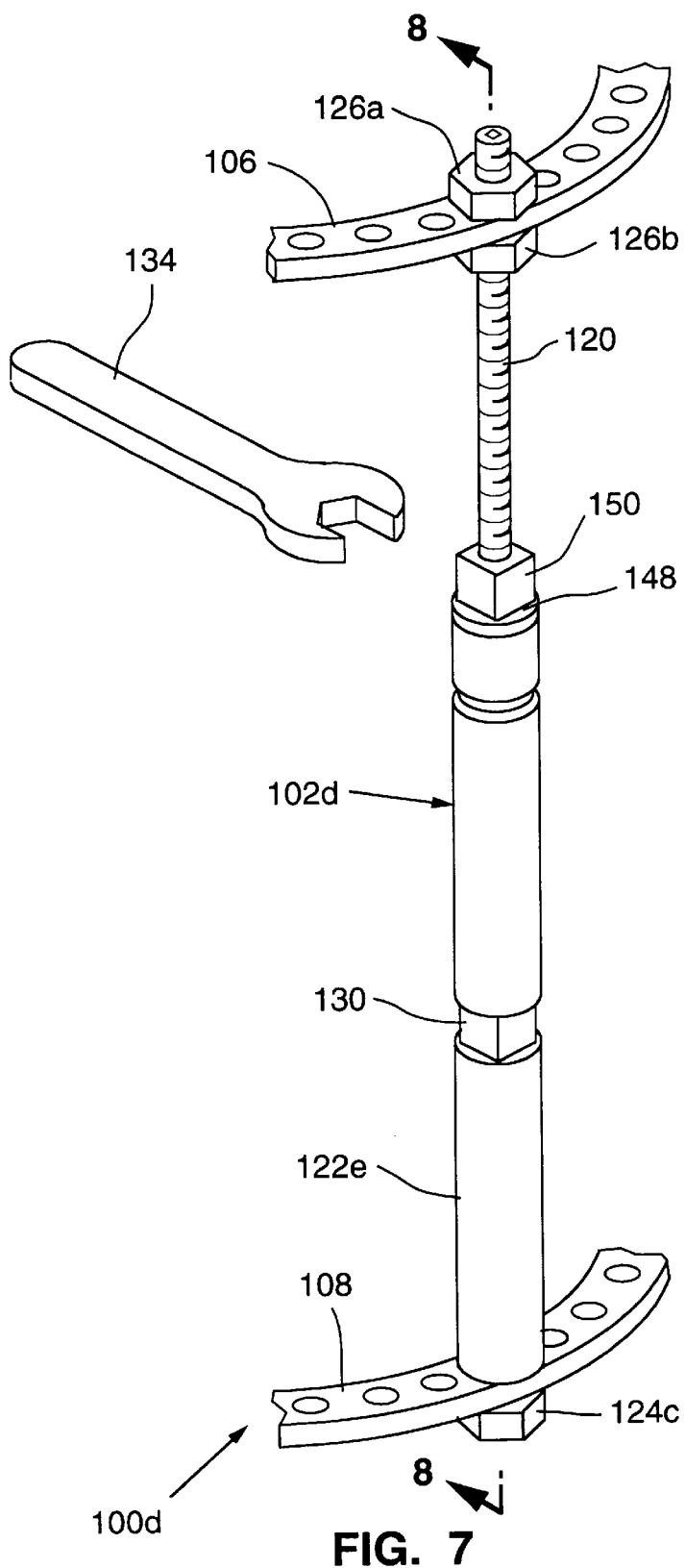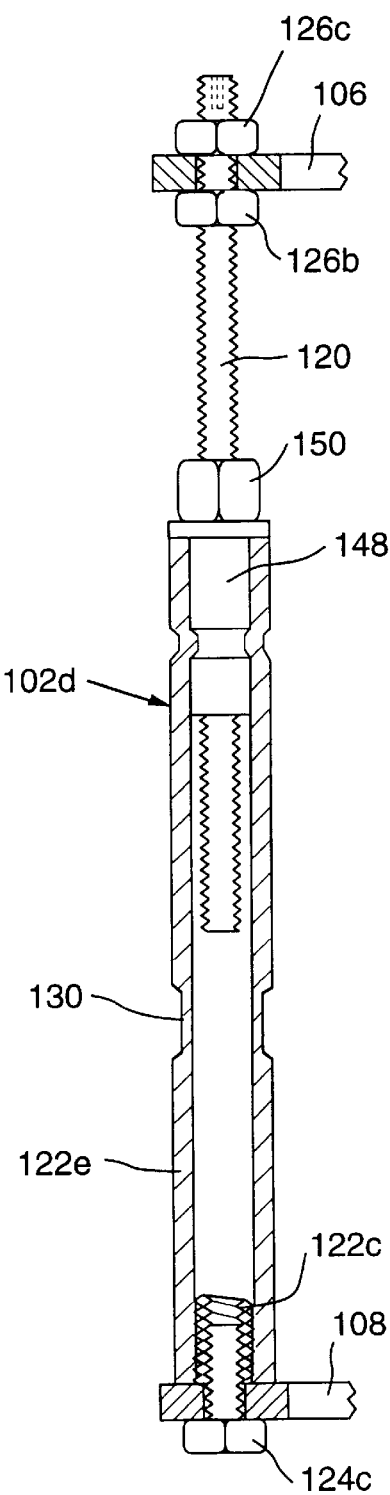
FIG. 7   FIG. 8

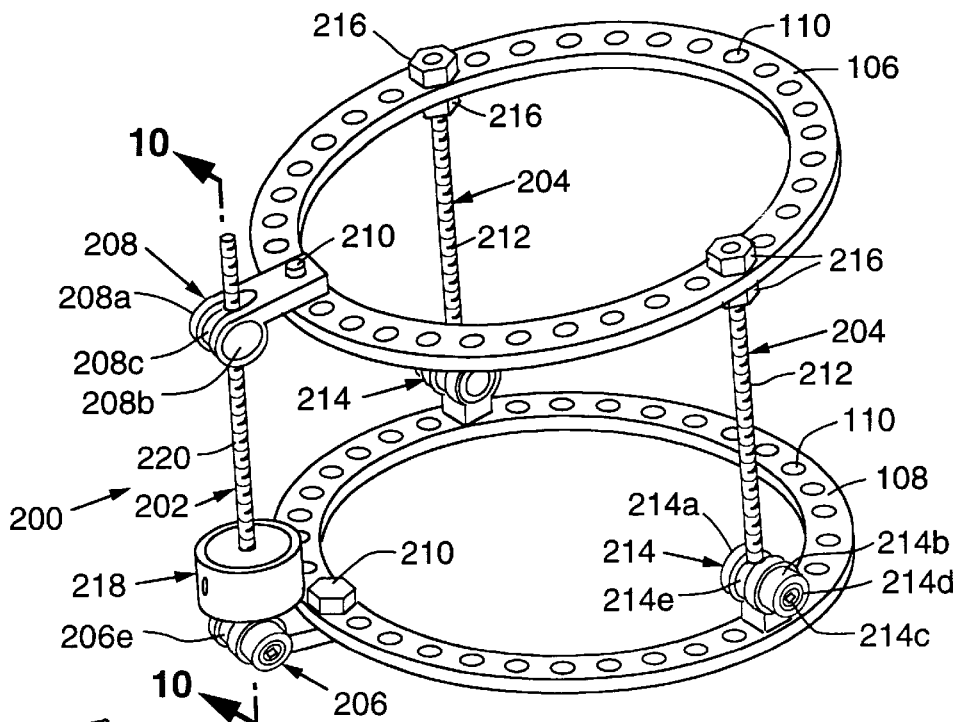
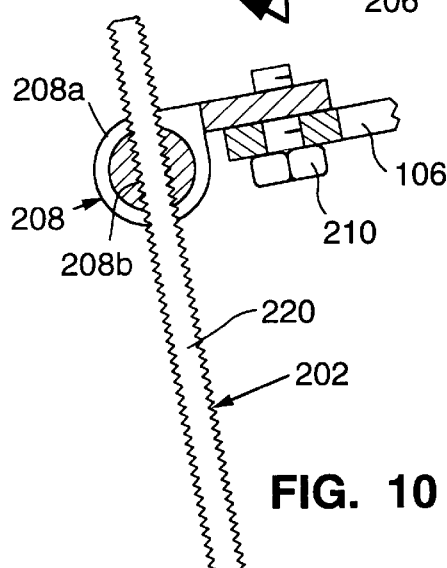
FIG. 9
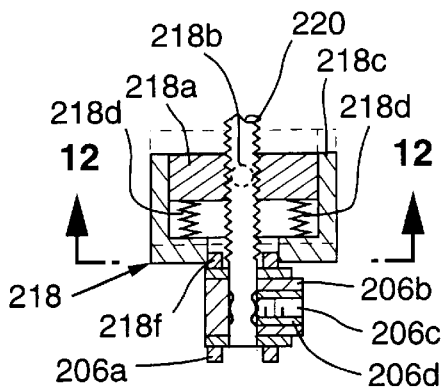
FIG. 11
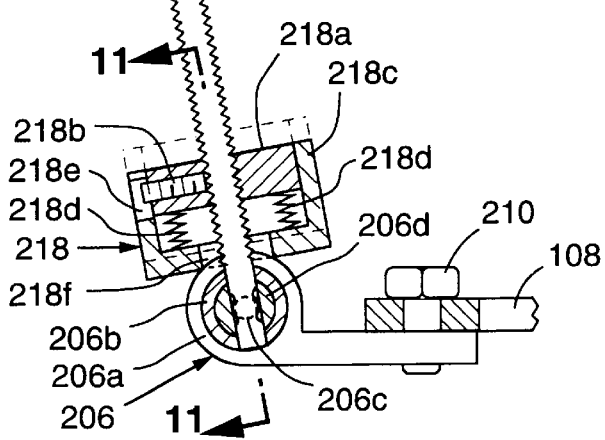
FIG. 10
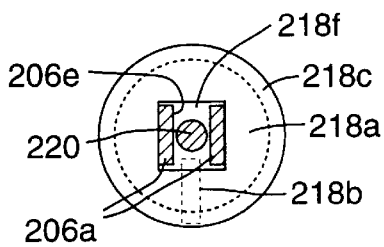
FIG. 12

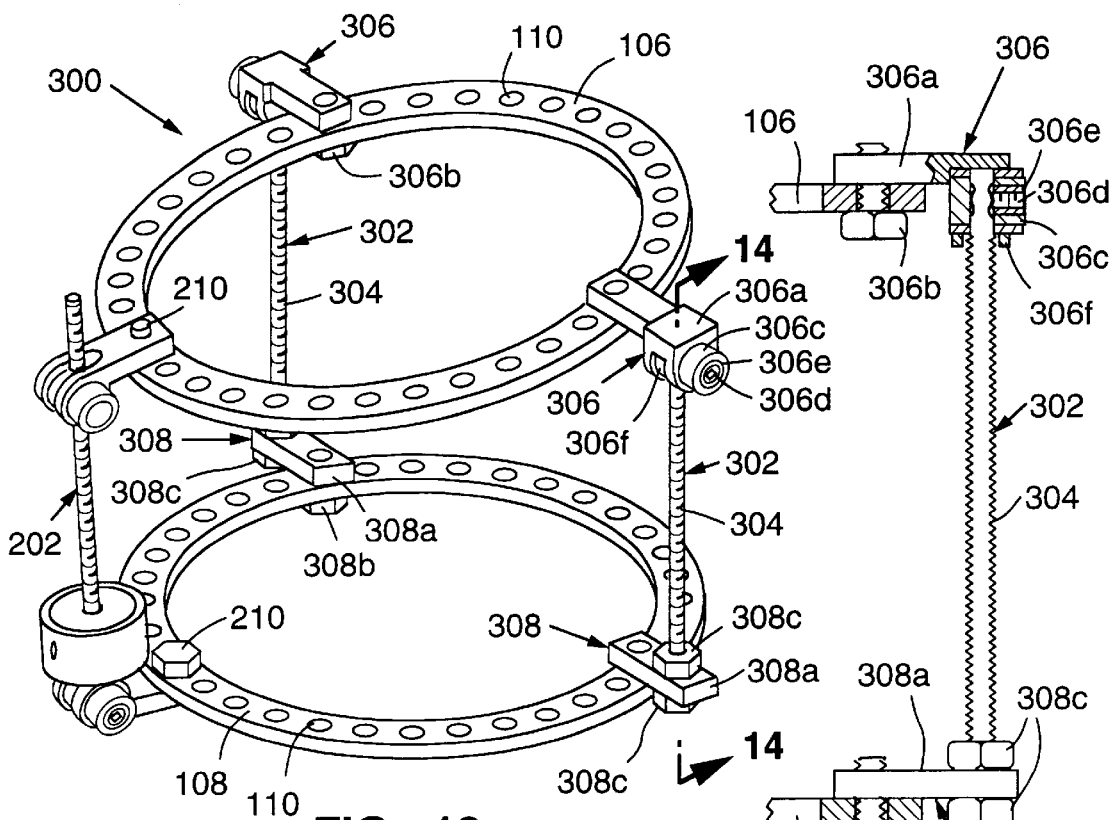
FIG. 13
FIG. 14
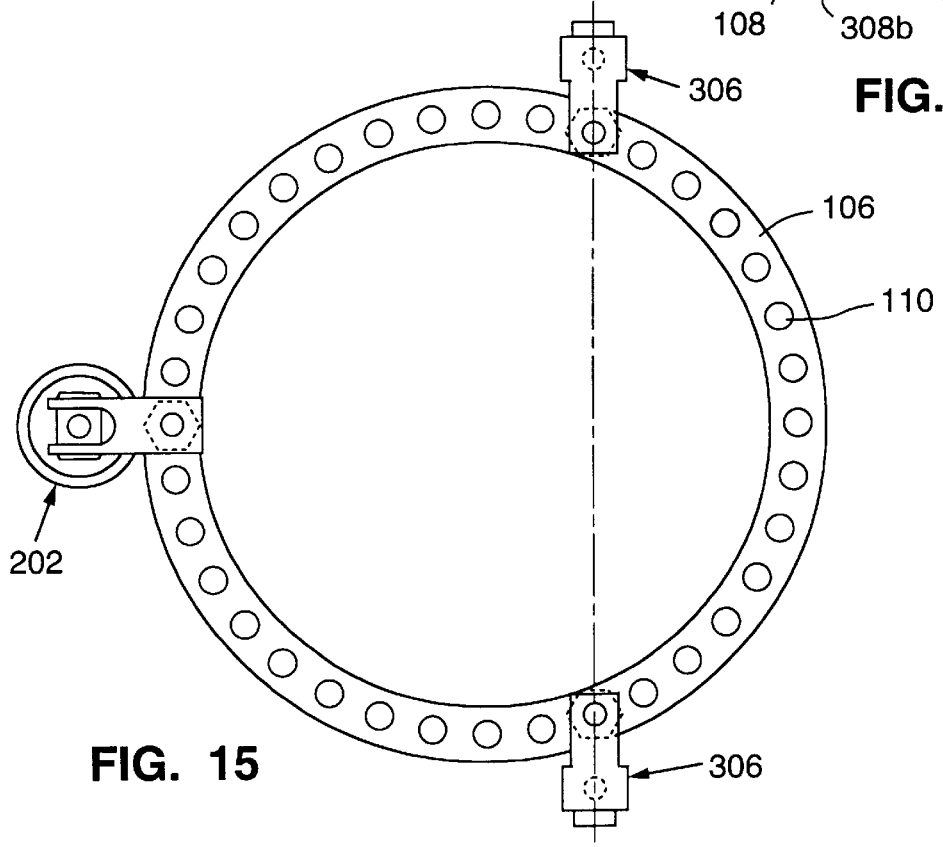
FIG. 15

PLASTIC DOUBLE NUT MECHANISM ENABLING RIGID ORTHOPEDIC DISTRACTION

RELATED APPLICATIONS

The application is a continuation of U.S. application Ser. No. 08/448,922, filed May 25, 1995, which is a divisional of abandoned U.S. application Ser. No. 08/075,179 filed Jun. 10, 1993.

BACKGROUND OF THE INVENTION

The present invention relates to external fixation devices, and in particular, to distractor mechanisms and hinges for external fixation devices.

External fixation of bone fractures is well known in the art. Many different external fixation devices have been developed, virtually all of which in one form or another use multiple transverse fixation wires or half-pins which extend through, or are embedded in, respectively, the bone and soft tissue surrounding the bone, and connect to various types of supporting elements, such as rings, half-rings, arches or bars.

Aside from providing stable fixation of bone fragments to promote proper fracture healing, external fixation devices also provide means for transporting the bone fragments in order to correct length discrepancies or angular deformities of the bone. One of the more common external fixation devices used for such purposes, often referred to as the Ilizarov External Fixator, includes three basic elements: multiple rings (or arches) disposed coaxially about the bone segments to be fixated; transverse wires or half-pins for fixating the bone segments to the rings (or arches); and distractor mechanisms. For angular distraction, the external fixator further includes pivots, or hinges, to define an axis of rotation perpendicular to the plane of the bone deformity to allow rotation of the bone segment.

Hence, for linear distraction, a typical basic assembly includes proximal and distal rings, or ring sets, connected by three or four distractor mechanisms; and for angular distraction, a typical basic assembly includes proximal and distal rings, or ring sets, connected by two hinges and one distractor mechanism.

A conventional distractor mechanism for linear distraction consists of a threaded rod which is fastened to each of the rings by the use of double nut assemblies, i.e. nuts which are threaded onto the rod and tightened against either side of each ring. A conventional distractor mechanism for angular distraction consists of two hinge segments which are fastened to the proximal and distal rings, and are coupled to each other via a threaded distraction rod. A conventional basic hinge assembly used for angular distraction consists of two hinge segments which are fastened directly to the rings and connected to each other with a nut and bolt.

The current conventional external fixator elements (distractors and hinges) present a number of problems. First, because the connection points for the distractor mechanisms and hinge assemblies, i.e. the holes in the rings and hinge members, must be slightly larger than the diameter of the threaded component (rods and bolts), the resulting assembly is always unstable. In other words, during installation, adjustment or distraction, a certain amount of mechanical "free play" will be present. During the treatment period of the patient, this can and often does cause pain.

Currently, there are two methods used in seeking to compensate for this problem. One method is to loosen and retighten all hinge and distractor nuts before and after each angular correction or linear distraction maneuver. This can be effective, but is time consuming and frustrating for the patient. Plus, the torque which must be applied to loosen and retighten the hardware can adversely affect the healing process and cause pain for the patient. The second method involves the use of nylock nuts in the hinges and distractor mechanisms to achieve some degree of radial stability by imposing an axial preload on the rotating elements. The mechanical "free play" is still there, but is damped by frictional forces from the fasteners. However, even when the hinge is precisely adjusted, the potential for an unstable frame is still present due to the over-sized hole diameters.

A second problem arises during each distraction maneuver, particularly during an angular distraction. Each incremental distraction takes a great deal of time, and the procedure is generally too complex for young patients to perform reliably. With so many components, i.e. plates, hinge segments, rods, bolts and nuts, to loosen, turn and retighten, it is difficult for the patient to remember the adjustment sequence and maintain a consistent distraction rate. Moreover, if any of the nuts are accidentally left untightened, instability, and therefore, pain and delayed healing, can result.

Accordingly, it would be desirable to have an external fixation device with a distraction mechanism which allows adjustable distraction while simultaneously providing a rigid structure, i.e. both radial and axial stability of the overall assembly.

SUMMARY OF THE INVENTION

A linear distractor mechanism in accordance with a preferred embodiment of the present invention includes a single-threaded screw distractor and a rotatable connector. The single-threaded screw distractor connects to the proximal and distal external fixator frame members, and rigidly and adjustably disposes the external fixator frame members at a separation distance which is linearly adjustable. The rotatable connector rotatively connects the single-threaded screw distractor to one of the external fixator frame members. The interconnected single-threaded screw distractor, rotatable connector and external fixator frame members form a rigid structure with a rigidity which is maintained during the adjusting of the separation distance between the frame members.

A preferred embodiment of the single-threaded screw distractor is a telescoping assembly with a single-threaded rod and a like-threaded, rotatable, coaxial sleeve. A preferred embodiment of the rotatable connector is a fastener assembly with a bolt and a pair of plastic washers, wherein the plastic washers are disposed on opposing sides of one of the external fixator frame members and the bolt extends therethrough and threads into the single-threaded screw distractor. An alternative preferred embodiment of the rotatable connector is a fastener assembly with a pair of threaded, plastic nuts, wherein the threaded, plastic nuts are disposed on opposing sides of one of the external fixator frame members and the single-threaded screw distractor extends and threads therethrough.

A linear distractor mechanism in accordance with an alternative preferred embodiment of the present invention includes a rod, base and adjustable connector. The rod connects to one and the base connects to the other of the external fixator frame members. The adjustable connector adjustably connects the rod to the base to rigidly and adjustably dispose the external fixator frame members at a separation distance which is linearly adjustable. The interconnected rod, base, adjustable connector and external fixator frame members form a rigid structure with a rigidity which is maintained during the adjusting of the separation distance between the frame members.

A preferred embodiment of the rod is a threaded rod. A preferred embodiment of the base is a hollow sleeve for coaxially receiving the rod. A preferred embodiment of the adjustable connector is a plastic fastener assembly with a pair of threaded plastic nuts for disposition on opposing sides of an extended portion of the base with the rod extending and threading therethrough. An alternative preferred embodiment of the adjustable connector is a fastener assembly with a bracket coupled to the base and a pair of threaded plastic nuts for disposition on opposing sides of a portion of the bracket with the rod extending and threading therethrough. Another alternative preferred embodiment of the adjustable connector is a plastic fastener assembly with a threaded plastic member rotatably captured within the base for threaded engagement with one end of the rod.

An angular distractor assembly in accordance with the present invention includes a distractor, a pair of pivotable connectors, and a pair of pivotable spacers. The distractor, via the pivotable connectors, connects the proximal and distal external fixator frame members, and rigidly and adjustably disposes the frame members at an angular orientation with respect to one another. One pivotable connector pivotally connects a portion of the distractor to one of the external fixator frame members, and another pivotable connector pivotally connects another portion of the distractor to the other frame member. The pivotable spacers pivotally connect and separate the external fixator frame members. The interconnected distractor, pivotable connectors, pivotable spacers and external fixator frame members form a rigid structure with a rigidity which is maintained during adjustment of the angular orientation between the frame members.

A preferred embodiment of the distractor is a single-threaded, rotatable rod which is rotatively engaged with one of the pivotable connectors and threadedly engaged with the other pivotable connector. A preferred embodiment of the pivotable connector is a metal and plastic pivot assembly including a metal bracket with a pivotable, plastic insert. A preferred embodiment of the pivotable spacer is a metal spacer and a metal and plastic pivot assembly. The metal spacer includes a rod with a portion for engaging the metal and plastic pivot assembly and another portion for connecting to one of the external fixator frame members. The metal and plastic pivot assembly includes a metal bracket for connecting to the other external fixator frame member and a pivotable, plastic insert for engaging the rod.

These and other features and advantages of the present invention will be understood upon consideration of the following detailed description of the invention and the accompanying drawings.

BRIEF DESCRIPTION OF THE DRAWINGS

FIGS. 3A and 3B illustrate a ratchet assembly which can be used on the linear distractor mechanisms of FIG. 1.

FIG. 5 illustrates a further alternative preferred embodiment of a linear distractor assembly in accordance with the present invention.

FIG. 6 illustrates a cross-section (along line 6—6) of the linear distractor mechanism of FIG. 5.

FIG. 7 illustrates a still further alternative preferred embodiment of a linear distractor assembly in accordance with the present invention.

FIG. 8 illustrates a cross-section (along line 8—8) of the linear distractor mechanism of FIG. 7.

FIG. 9 illustrates an external fixator with an angular distractor assembly in accordance with an alternative preferred embodiment of the present invention.

FIG. 10 illustrates a cross-section (along line 10—10) of the angular distractor mechanism of FIG. 9.

FIG. 11 illustrates a cross-section (along line 11—11) of the adjustor mechanism on the angular distractor mechanism of FIG. 10.

FIG. 12 illustrates a cross-section (along line 12—12) of the adjustor mechanism of FIG. 11.

FIG. 13 illustrates an external fixator with an angular distractor assembly in accordance with an alternative preferred embodiment of the present invention.

FIG. 14 illustrates a cross-section (along line 14—14) of one of the pivotable spacer mechanisms of FIG. 13.

FIG. 15 illustrates a top view perpendicular to the plane of the upper frame member of the external fixator of FIG. 13.

DETAILED DESCRIPTION OF THE INVENTION

Figure 1:
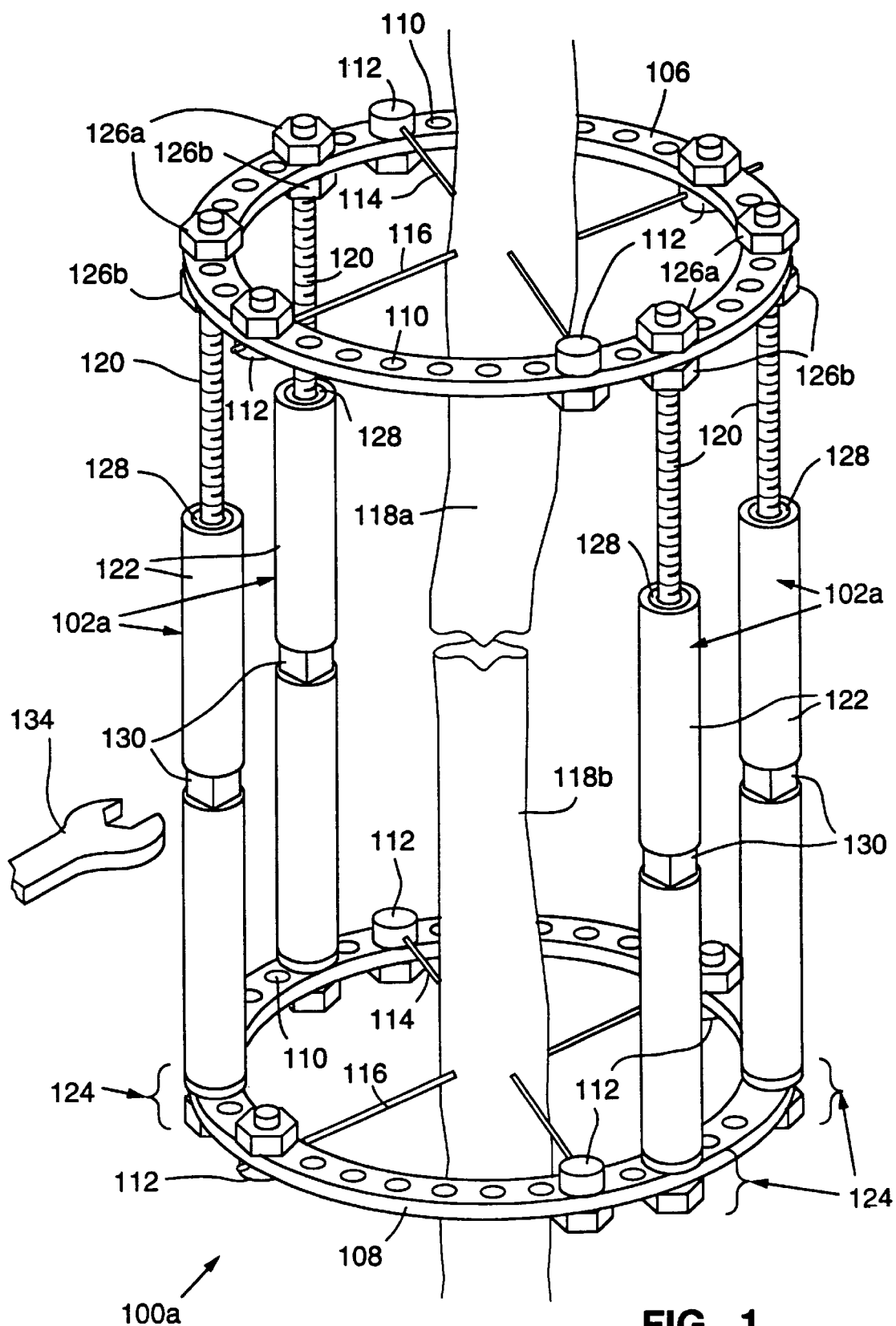
FIG. 1 illustrates an external fixator with a preferred embodiment of a linear distractor assembly in accordance with the present invention.

Referring to FIG. 1, an external fixator assembly 100a for performing linear distraction with a preferred embodiment of a linear distractor assembly in accordance with the present invention includes linear distractor mechanisms 102a, and upper 106 and lower 108 external fixator frame members, or rings. Each ring 106, 108 includes multiple, spaced holes 110, a number of which are used for mounting fastener assemblies 112 (discussed further below) for fastening transverse wires 114 and/or half-pins 116. These wires 114 and/or half-pins 116 pass through or are anchored into, respectively, the bone segments 118a, 118b which are to be externally fixated with the fixator assembly 100a.

Each distractor mechanism 102a includes a single-threaded rod 120 which is coaxially mated with an internally like-threaded, plastic insert 128 mounted within a rotatable sleeve 122. The rod 120 is fastened to the upper ring 106 by extending it through one of the holes 110 and having two nuts 126a, 126b tightened against opposing sides of the ring 106. The sleeve 122 is rotatively connected to the lower ring 108 by way of a rotatable connector 124 (discussed further below). At approximately the midway point of the sleeve 122, is a recessed, square portion 130 which can be used as a tool interface for mating with a tool (e.g. a wrench 134) for rotating the sleeve 122.

Figure 3A:
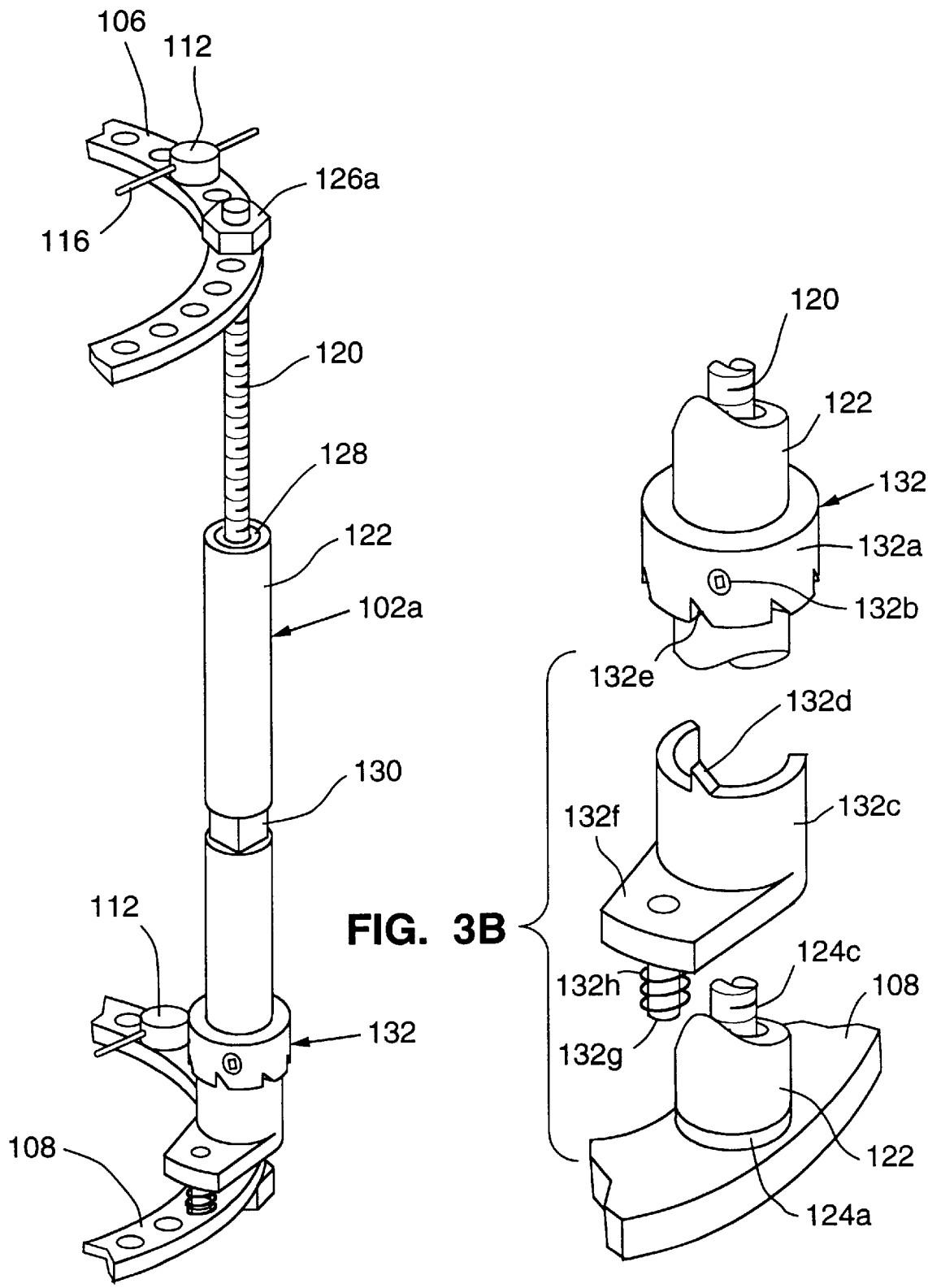

The distractor mechanisms 102a can also include a ratchet assembly 132 (as shown in FIGS. 3A and 3B, and discussed further below). This ratchet assembly 132 prevents rotation of the sleeve 122 in a selected direction.

Figure 2:
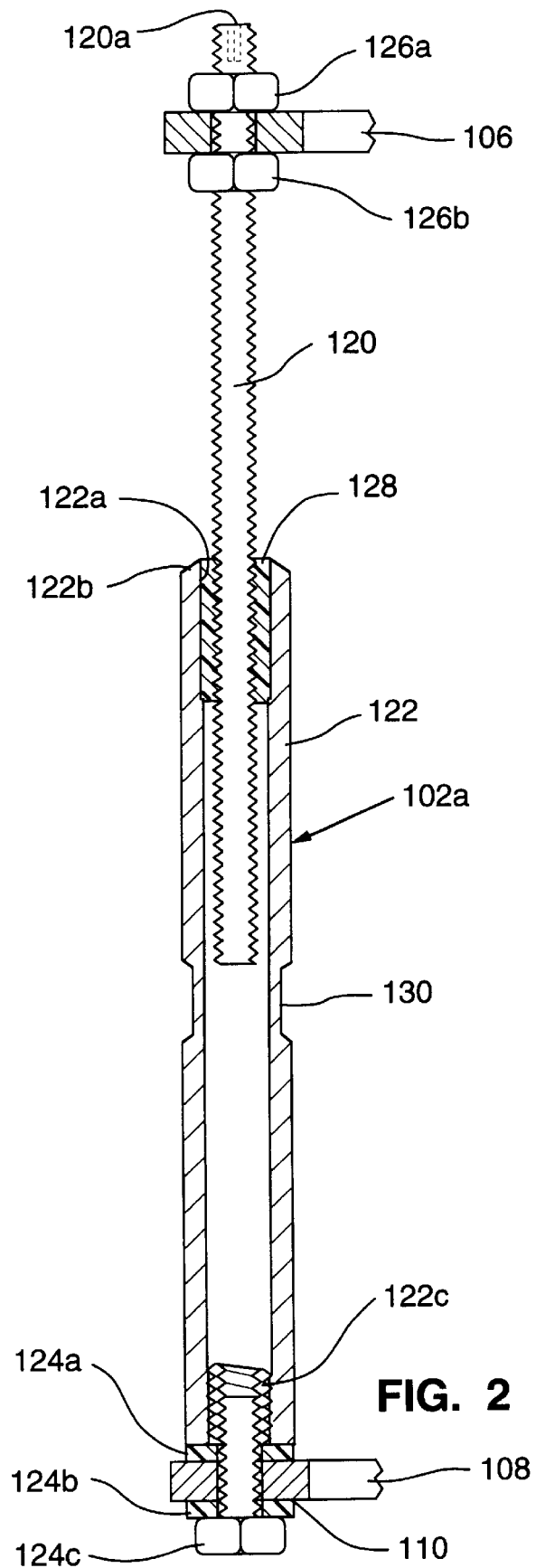
FIG. 2 illustrates a cross-section (along line 2—2) of one of the linear distractor mechanisms of FIG. 1.

Referring to FIG. 2, the construction of a linear distractor mechanism 102a in accordance with the present invention can be understood. The metal-to-plastic interface of the threaded rod 120 and like-threaded plastic insert 128 can be seen in cross-section. The plastic insert 128 is pressed into the end 122a of the rotatable sleeve 122 which is counterbored, and is prevented from rotating within or being pulled out from the sleeve 122 by crimping the tip 122b of the sleeve 122 (e.g. in a pyramidal shape) after the insert 122 has been pressed therein.

Referring still to FIG. 2, the rotatable connector 124 can be better understood. The rotatable sleeve 122 is connected to the bottom ring 108 by placing plastic washers 124a and 124b on opposite sides of the ring 108, and passing a bolt 124c through the ring hole 110 and plastic washers 124a, 124b to be mated with internal locking threads 122c (e.g. screw thread inserts produced under the trademark HELI-COIL®) of the sleeve 122. The bolt 124c is then tightened down within the sleeve 122 and against the plastic washers 124a, 124b to eliminate any axial free play between the ring 108 and sleeve 122. These internal locking threads 122c prevent the bolt 124c from turning independently from the sleeve 122. This prevents the union of the bolt 124c and sleeve 122 from becoming overly tight (which would inhibit rotation of the sleeve 122) or loose (which would introduce undesirable axial free play between the ring 108 and sleeve 122). The plastic washers 124a, 124b are compressed by the tightened bolt 124c and significantly reduce friction, thereby assisting in setting and maintaining an appropriate preload between the metal bolt 124c, rotatable sleeve 122 and ring 108.

Due to the metal-to-plastic interfaces of the sleeve 122, plastic washer 124a and ring 108, and of the bolt 124c, plastic washer 124b and ring 108, the sleeve 122 can be selectively rotated while simultaneously forming and maintaining a rigid structure with respect to the lower ring 108. This rigidity is further maintained by the metal-to-plastic interface of the threaded rod 120 and plastic insert 128, as the metal rod 120 remains fixed, and therefore rigid, with respect to the upper ring 106.

The threaded rod 120 has a hexagonal socket 120a in the end to facilitate rotation of the rod 120 into or out of the sleeve 122 by use of a conventional hexagonal key wrench (not shown). Such adjustments are often necessary when initially adjusting or attaching a linear distractor mechanism 102a to the rings 106, 108, since the interface between the plastic insert 128 and the threaded rod 120 is sufficiently tight as to require more than finger pressure on the rod 120 to rotate it into and out of the sleeve 122. However, the larger diameter of the rotatable sleeve 122 provides sufficiently greater leverage that ordinary finger pressure is sufficient to rotate the sleeve 122 on the rod 120 once the rod 120 is secured to the ring 106 with the nuts 126a, 126b.

Referring to FIGS. 3A and 3B, the ratchet assembly 132 can be better understood. The ratchet assembly 132 includes a circular collar 132a, which is fixed about the rotatable sleeve 122 via compression with a hexagonal socket set screw 132b. This circular collar 132a sits atop an arcuate collar 132c which is also coaxial with the sleeve 122. This arcuate collar 132c has a unidirectionally sloped tooth 132d which engages similarly shaped notches 132e in the lower edge of the circular collar 132a. A flange 132f extending from the arcuate collar 132c has a downwardly extending pin 132g which engages a hole 110 in the lower ring 108. A helical spring 132h wound coaxially about this pin 132g upwardly biases the arcuate collar 132c. Thus, as the sleeve 122, and therefore the circular collar 132a, is rotated, the mating tooth 132d and notches 132e allow the sleeve 122 to rotate in one direction only.

This ratchet assembly 132 advantageously allows the sleeve 122 to be rotated in calibrated amounts, e.g. by listening for the "clicks" made as the tooth 132d snaps into place when engaging one of the notches 132e as the sleeve 122 is rotated. This allows the user of the external fixator 100a to make calibrated adjustments of the distractor mechanism 102a without the aid of tools and without the need for counting fractional revolutions of the sleeve 122. Instead, the number of clicks can be counted to determine if and when sufficient adjustment has been made.

Figure 4:
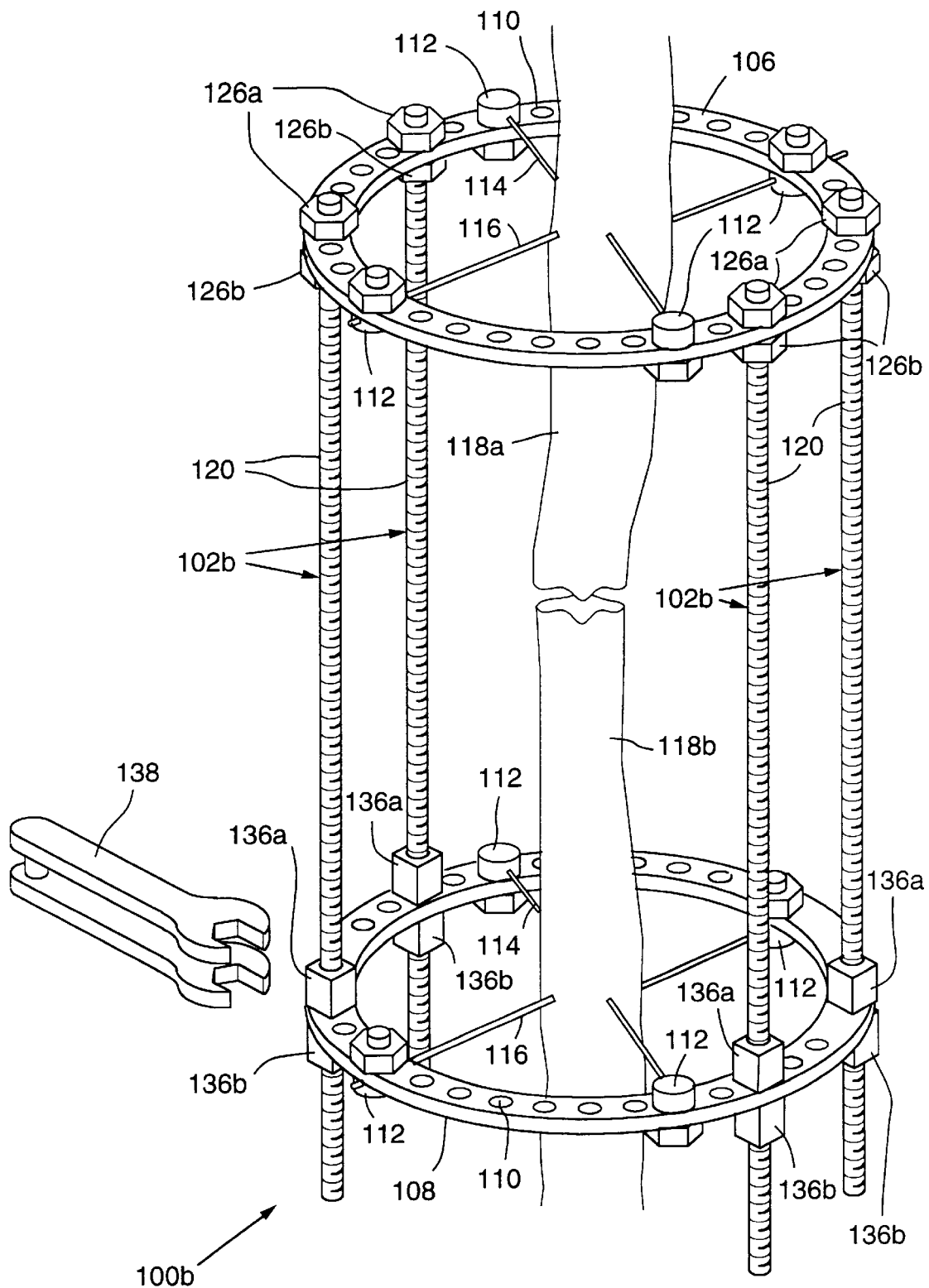
FIG. 4 illustrates an external fixator with an alternative preferred embodiment of a linear distractor assembly in accordance with the present invention.

Referring to FIG. 4, an external fixator assembly 100b for performing linear distraction with an alternative preferred embodiment of a linear distractor assembly in accordance with the present invention includes linear distractor mechanisms 102b of an alternative type, and upper 106 and lower 108 external fixator frame members, or rings, as discussed above. This type of linear distractor mechanism 102b is particularly useful in those cases where the initial, or starting, distance between the rings 106, 108 and the amount of lengthening are small. In such cases, the single-threaded rod 120 is secured to one ring 106 with two nuts 126a, 126b, as discussed above, and is passed through a hole 110 in the other ring 108 and is secured thereto with two plastic prevailing torque lock nuts 136a, 136b which are tightened against opposing sides of the ring 108. The faces of the plastic nuts 136a, 136b are aligned for simultaneous interfacing with and turning in the desired direction by a double wrench 138.

Referring to FIGS. 5 and 6, an external fixator assembly 100c for performing linear distraction with another alternative preferred embodiment of a linear distractor assembly in accordance with the present invention includes linear distractor mechanisms 102c of an alternative type, and upper 106 and lower 108 external fixator frame members, or rings, as discussed above. Each distractor mechanism 102c includes the single-threaded rod 120 which is coaxial with a nonrotating sleeve 122d. The nonrotating sleeve 122d serves as a stationary base member and is connected to the lower ring 108 with a bolt 124c which mates with the internal locking threads 122c. A metal C-shaped bracket 140, which includes a metallic adjustment surface, is connected to the other end of the nonrotating sleeve 122d with its internally threaded bushing end 142 mating with an externally threaded portion of the nonrotating sleeve 122d.

One end of the single-threaded rod 120 is secured to the upper ring 106 with two nuts 126a, 126b, as discussed above. The other end of the single-threaded rod 120 extends through holes 146, 144 in the top portion and bushing end 142 of the bracket 140, and is secured to the bracket 140 with a pair of plastic prevailing torque lock nuts 136a, 136b which are tightened against opposing sides of the top portion of the bracket 140. The faces of the plastic nuts 136a, 136b are preferably aligned for simultaneous interfacing with and rotation by the aforementioned double wrench 138.

Referring to FIGS. 7 and 8, an external fixator assembly 100d for performing linear distraction with still another alternative preferred embodiment of a linear distractor assembly in accordance with the present invention includes linear distractor mechanisms 102d of an alternative type, and upper 106 and lower 108 external fixator frame members, or rings, as discussed above. Each distractor mechanism 102d includes the single-threaded rod 120 which is coaxial with a nonrotating sleeve 122e. The nonrotating sleeve 122e serves as a stationary base member and is connected to the lower ring 108 with a bolt 124c which mates with the internal locking threads 122c.

One end of the single-threaded rod 120 is secured to the upper ring 106 with two nuts 126a, 126b, as discussed above. The other end of the single-threaded rod 120 extends and threads into a threaded, rotatable plastic insert 148 within the nonrotating sleeve 122e. The plastic insert 148 is captured within the nonrotating sleeve 122e and prevented from being withdrawn therefrom by crimping the sleeve 122e after the insert 148 has been pressed therein. The plastic insert 148 includes a shaped (e.g. square) portion 150 which can be used as a tool interface for mating with the aforementioned wrench 134.

As should be evident from the foregoing, the metal-to-plastic interfaces between the rod 120, bracket 140 and plastic nuts 136a, 136b (FIG. 5), and between the rod 120, sleeve 122e and plastic insert 148 (FIG. 7), allow the plastic nuts 136a, 136b and plastic insert 148 to be selectively rotated while simultaneously forming and maintaining a rigid structure with respect to the upper 106 and lower 108 rings.

Referring to FIG. 9, an external fixator 200 for performing angular distraction with a preferred embodiment of an angular distractor assembly in accordance with the present invention includes upper 106 and lower 108 external fixator rings (as discussed above), an angular distractor mechanism 202, and two pivotable, or hinged, spacer mechanisms 204. The upper 106 and lower 108 rings have an angular orientation with respect to one another which is determined by the distractor mechanism 202 and pivotable spacer mechanisms 204.

Each pivotable spacer mechanism 204 includes a threaded rod 212 which is fastened to the upper ring 106 by two nuts 216 tightened on opposing sides thereof. The bottom of the threaded rod 212 includes a spherical profile and is anchored in a pivotable connector assembly 214, which in turn is fastened to the bottom ring 108 by a bolt (not shown) threaded into its underside through a hole 110 of the bottom ring 108.

The pivotable connector assembly 214 includes a metal frame 214a with a plastic insert 214b. A set screw 214d is tightened snugly against the spherically-profiled portion (or "ball") of the threaded rod 212 to hold it in place within the plastic insert 214b. For additional strength as desired, the plastic insert 214b can include a metal core 214c into which the set screw 214d is threaded. The threaded rod 212 protrudes through a circumferential slot 214e in the metal frame 214a. This allows the threaded rod 212 to pivot along an arc extending outwardly from the pivot axis formed by the longitudinal axis of the plastic insert 214b (i.e. coaxial with the set screw 214d).

The angular distractor mechanism 202 includes a single-threaded rod 220 which is coupled to the top ring 106 by an upper pivotable connector assembly 208, and coupled to the lower ring 108 by a lower pivotable connector assembly 206. The upper 208 and lower 206 pivotable connectors (discussed further below) are fastened to the upper 106 and lower 108 rings by bolts 210. As discussed further below, a rotatable knob 218 is affixed to and used to rotate the threaded rod 220. This causes the upper pivotable connector 208, which is threaded onto the rod 220, to travel along the length of the rod 220. This, in turn, causes the upper 208 and lower 206 pivotable connectors to be selectively drawn closer together or further apart. This action, in conjunction with the pivoting action of the pivotable spacers 204, allows the angular orientation between the upper 106 and lower 108 rings to be adjusted. The pivotable spacers 204 are mounted on the lower ring 108 so as to make their pivotal axes collinear with one another.

Referring to FIG. 10, the angular distractor mechanism 202 can be better understood. As shown, the threaded rod 220 is threaded into a plastic insert 208b which is captured within the metal frame 208a of the upper pivotable connector 208. The frame 208a has a circumferential slot 208c (FIG. 9) to allow arcuate movement of the threaded rod 220 as it and the plastic insert 208b rotate within the frame 208a during distraction adjustments.

The bottom of the threaded rod 220 (with the spherically-profiled, or "ball", portion) is inserted into and anchored within a plastic spacer 206b captured within the metal frame 206a of the lower pivotable connector 206. The bottom of the threaded rod 220 is anchored within the plastic spacer 206b by way of a hex-socket set screw 206c which is threaded into the plastic insert 206b (which can include a metal core 206d for additional strength). As discussed further below, the set screw 206c has a cup-shaped tip which engages the base of the rod 220 and allows the rod 220 to rotate about its longitudinal axis within the plastic insert 206b. Similar to the upper pivotable connector 208, the lower pivotable connector frame 206a has a circumferential slot 206e (FIG. 9) which allows arcuate movement of the threaded rod 220 during distraction adjustments.

Referring to FIGS. 10, 11 and 12, the rotatable knob 218 has an inner coaxial plate 218a which is fixed to the threaded rod 220 via compression with a hex-socket set screw 218b. A coaxial sleeve 218c, surrounding the plate 218a, is biased downwardly by two springs 218d but can be pulled upwardly, due to an elongated clearance hole, or slot, 218e for the set screw 218b.

When biased downwardly by the springs 218d, the sleeve 218c sits atop the upper portion of the frame 206a of the lower pivotable connector 206. A square hole 218f prevents this sleeve 218c from being rotated when in this position.

Referring to FIG. 13, an external fixator 300 for performing angular distraction with an alternative preferred embodiment of an angular distractor assembly in accordance with the present invention includes upper 106 and lower 108 external fixator rings (as discussed above), an angular distractor mechanism 202 (as discussed above), and pivotable spacer mechanisms 302.

Referring to FIGS. 13 and 14, each of the pivotable spacer mechanisms 302 includes a threaded rod 304, a pivotable connector 306 and bracket assembly 308. The rod 304 is fastened to the lower ring 108 with the bracket assembly 308, which consists of a bracket frame 308a, a bolt 308b and two nuts 308c. The rod 304 is pivotally connected to the upper ring 106 by the pivotable connector 306. The pivotable connector 306 includes a metal frame 306a which is fastened to the upper ring 106 by a bolt 306b. The upper end of the rod 304 is anchored within a plastic insert 306c captured within the metal frame 306a by way of hex-socket set screw 306d which is threaded through the plastic insert 306c (which can include a metal core 306e for additional strength). The metal frame 306a includes a circumferential slot 306f to allow arcuate movement of the rod 304 during distraction adjustments.

Referring to FIG. 15, the pivotable connectors 306 are aligned with one another so as to make their axes of rotation collinear with one another.

Due to the metal-to-plastic interfaces of the rods 212, 220 (FIG. 9), 304 (FIG. 13) and connectors 206, 208, 214 (FIG. 9), 306 (FIG. 13), angular distraction adjustments can be made while simultaneously forming and maintaining a rigid structure with respect to the interconnected upper 106 and lower 108 rings.

In accordance with the present invention, the threaded rods 120 (FIGS. 1, 5 and 7), 212 (FIG. 9), 220 (FIG. 9) and 304 (FIG. 13) are metal, preferably stainless steel. The rotatable sleeve 122 (FIG. 1) and nonrotating sleeves 122d, 122e (FIGS. 5 and 7) are metal, preferably aluminum. The various plastic inserts 128 (FIG. 1), 148 (FIG. 7), 208b, 214b (FIG. 9), 206b (FIG. 10), 306c (FIG. 13), plastic washers 124a, 124b (FIG. 2), and plastic nuts 136a, 136b (FIGS. 4 and 5) are preferably nylon (e.g. Nylon 6/6) polyphenylene sulfide, polyamid or polyimid. However, other plastics having similar resiliency qualities can be used as well.

Figure 16:
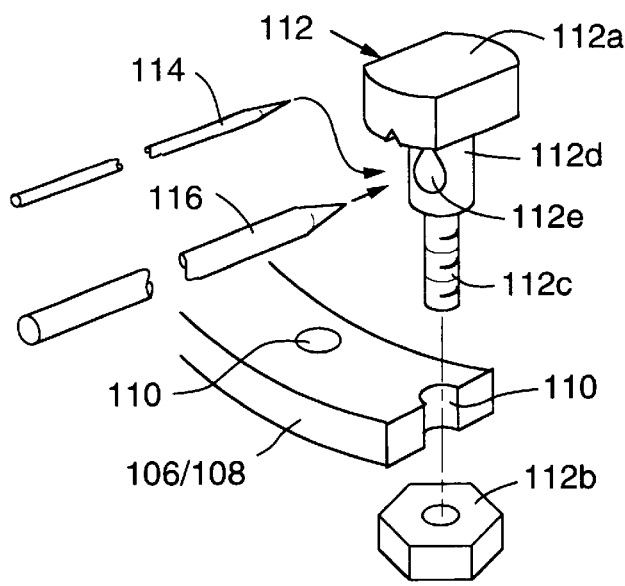
FIG. 16 illustrates the wire and pin fastener assembly used on the frame members of the external fixators of FIGS. 1, 4, 5, 7, 9 and 13.
Figure 17:
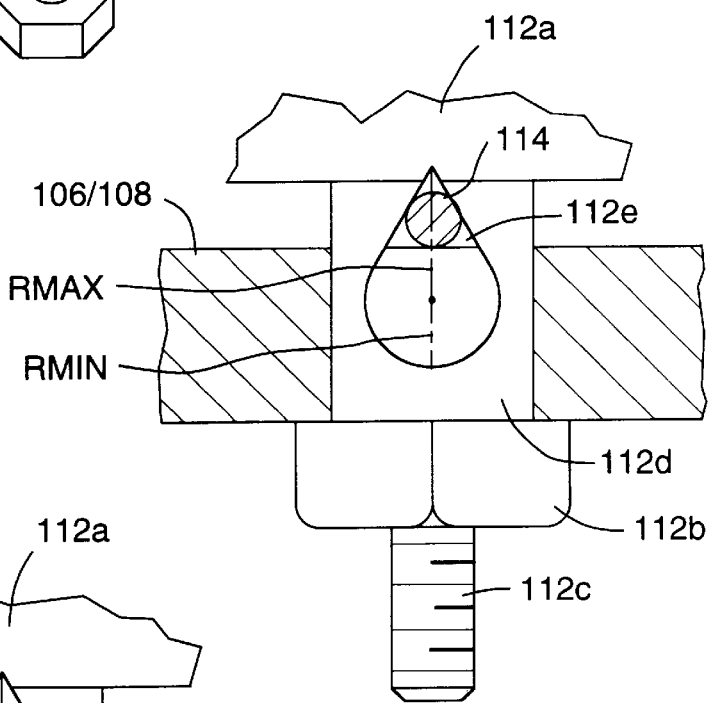
FIG. 17 illustrates a side view of the fastener assembly of FIG. 16 while fastening a wire to one of the external fixator frame members.
Figure 18:
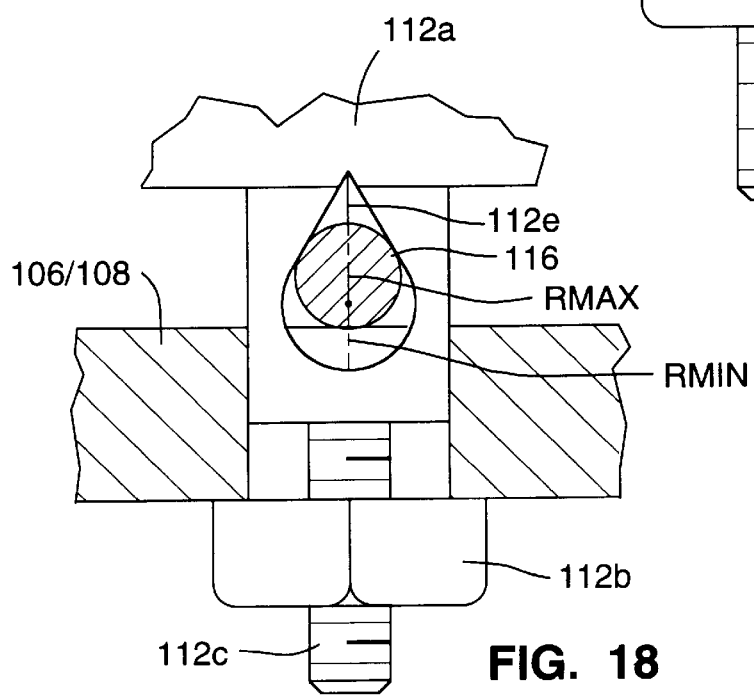
FIG. 18 illustrates a side view of the fastener assembly of FIG. 16 while fastening a pin to one of the external fixator frame members.

Referring to FIGS. 16, 17 and 18, the fastener assembly 112 for the wires 114 and/or half-pins 116 can be better understood. Each fastener assembly 112 includes a bolt 112a and a nut 112b. The bolt 112a has a threaded shaft 112c which is inserted through one of the holes 110 of the ring 106/108, and onto which is threaded and tightened the nut 112b. The bolt 112a also has a shank 112d with a transverse bore 112e. It is into this bore 112e that the wire 114 or larger diameter half-pin 116 is inserted.

The transverse shank bore 112e is asymmetrical with respect to the mounting surface for the fastener assembly 112, i.e. the plane of the ring 106/108. As can be seen, the bore 112e has a minimum radius RMIN and a maximum radius RMAX, with the minimum radius RMIN directed toward the threaded shaft 112c and the maximum radius RMAX directed toward the head of the bolt 112a. Preferably, the bore 112e is a teardrop-shaped hole as shown, but other asymmetrical shapes can be used as desired.

It can seen that such an asymmetrical hole 112e advantageously provides consistent contact surfaces for contacting and securing the wire 114 or half-pin 116, regardless of their diameters. Accordingly, the same fastener assembly 112 can be used for wires 114 and/or half-pins 116 having a large variety of diameters.

From the foregoing, it can be seen that the inboard pivots, or hinges, provided by the pivotable spacers 204 of FIG. 9 provide an axis of rotation which is parallel to the plane formed by the lower ring 108 and is located between the planes formed by the upper 106 and lower 108 rings. Further, it can be seen that the outboard pivots, or hinges, formed by the pivotable spacers 302 of FIG. 13 form an axis of rotation which lies approximately within the plane formed by the upper ring 106. Accordingly, it should be understood that various combinations of these inboard 204 and outboard 302 pivotable spacers can be used to perform various forms of angular distraction of bone segments. Additionally, it should be recognized that the terms "upper" and "lower" with respect to the two external fixator rings 106, 108 have been used for purposes of convenience only, and are not to be construed as limitations upon their actual location or orientation with respect to one another.

Various other modifications and alterations in the structure and method of operation of this invention will be apparent to those skilled in the art without departing from the scope and spirit of this invention. Although the invention has been described in connection with specific preferred embodiments, it should be understood that the invention as claimed should not be unduly limited to such specific embodiments.

We claim:

1. An external fixation device having a distraction mechanism, the external fixation device disposed to immobilize a bone fracture during distraction thereof, the distraction mechanism comprising:

first and second external fixator frame members separated by means for adjusting linear separation therebetween, said means for adjusting including:

a threaded rod, the threaded rod rigidly connected to the first external fixator frame member and extending towards the second fixator frame member, the threaded rod received into an opening in a metallic adjustment surface wherein telescopic displacement of the metallic adjustment surface with respect to the threaded rod causes corresponding adjustment of linear separation between the first and second external fixator frame members; and a pair of plastic nuts each threadably engaged on the threaded rod and disposed either side of the metallic adjustment surface, wherein tightening of the plastic nuts down on the metallic adjustment surface forms a rigid connection between the first and second external fixator frame members, and wherein synchronous co-rotation of the plastic nuts after said tightening adjusts linear separation between the first and second external fixator frame members without introducing play in said rigid connection between the first and second external fixator frame members.

2. The external fixation device of claim 1, in which the metallic adjustment surface is integral to the second external fixator frame member.

3. The external fixation device of claim 2, wherein said metallic adjustment surface is located on a C-shaped bracket.

4. The external fixation device of claim 3, wherein said C-shaped bracket is attached to a sleeve, with an internally threaded bushing end of said bracket mating with an externally threaded end of said sleeve, wherein said externally threaded end of said sleeve is distally located from said second external fixator frame member.

5. The external fixation device of claim 1, in which the second external fixator frame member has an extension rigidly connected thereto and extending towards the first external fixator frame member, and in which the metallic adjustment surface is located on the second external fixator frame member extension.

6. The external fixation device of claim 1, in which the plastic nuts have outer faces, and in which the outer faces of each plastic nut are aligned following said tightening to enable a double wrench to perform said synchronous co-rotation thereof.

7. The external fixation device of claim 1, wherein said rigid connection between said threaded rod and said first external fixator frame member comprises:

a hole in the first external fixator frame member, wherein said threaded rod is received therein; and a pair of nuts received onto said threaded rod and disposed on opposing sides of said first external fixator frame member.

8. An external fixation device having a distraction mechanism, the external fixation device disposed to immobilize a bone fracture during distraction thereof, the distraction mechanism comprising:

first and second external fixator frame members separated by means for adjusting linear separation therebetween, said means for adjusting including:

a threaded rod, the threaded rod rigidly connected to the first external fixator frame member and extending towards the second fixator frame member, the threaded rod received into an opening in a metallic adjustment surface integral to the second external fixator frame member wherein telescopic displacement of the metallic adjustment surface with respect to the threaded rod causes corresponding adjustment of linear separation between the first and second external fixator frame members; and a pair of plastic nuts each threadably engaged on the threaded rod and disposed either side of the metallic adjustment surface, wherein tightening of the plastic nuts down on the metallic adjustment surface forms a rigid connection between the first and second external fixator frame members, and wherein synchronous co-rotation of the plastic nuts after said tightening adjusts linear separation between the first and second external fixator frame members without introducing play in said rigid connection between the first and second external fixator frame members; and the plastic nuts further having outer faces, wherein the outer faces of each plastic nut are aligned following said tightening to enable a double wrench to perform said synchronous co-rotation thereof.

9. A method for distraction of a bone fracture, comprising the steps of:

(a) immobilizing a bone fracture with an external fixation device having first and second external fixator frame members; and (b) distracting the bone fracture by adjusting linear separation between the first and second external fixator frame members, wherein step (b) includes the substeps of:

(i) rigidly connecting a threaded rod to the first external fixator frame member and extending the threaded rod towards the second fixator frame member;

(ii) receiving the threaded rod into an opening in a metallic adjustment surface wherein telescopic displacement of the metallic adjustment surface with respect to the threaded rod causes corresponding adjustment of linear separation between the first and second external fixator frame members;

(iii) threadably engaging a pair of plastic nuts on the threaded rod;

(iv) disposing the plastic nuts either side of the metallic adjustment surface;

(v) forming a rigid connection between the first and second external fixator frame members by tightening the plastic nuts down on the metallic adjustment surface; and (vi) synchronously co-rotating the plastic nuts after said tightening to cause corresponding adjustment of linear separation between the first and second external fixator frame members without introducing play in said rigid connection between the first and second external fixator frame members.

10. The method of claim 9, in which the metallic adjustment surface is integral to the second external fixator frame member.

11. The method of claim 10, wherein said metallic adjustment surface is located on a C-shaped bracket.

12. The method of claim 11, further comprising the step of:

attaching said C-shaped bracket to a sleeve, with an internally threaded bushing end of said bracket mating with an externally threaded end of said sleeve, wherein said externally threaded end of said sleeve is distally located from said second external fixator frame member.

13. The method of claim 9, in which the second external fixator frame member has an extension rigidly connected thereto and extending towards the first external fixator frame member, and in which the metallic adjustment surface is located on the second external fixator frame member extension.

14. The method of claim 9, in which the plastic nuts have outer faces, and in which step (b) includes the further substep of:

(vii) aligning the outer faces of each plastic nut following said tightening to enable a double wrench to perform said synchronous co-rotation.

15. The method of claim 9, wherein said step of rigidly connecting said threaded rod to said first external fixator frame member further comprises the step of:

receiving said threaded rod through a hole in said first external fixator frame member; and threadably disposing a pair of nuts onto said threaded rod on opposing sides of said first external fixator frame member.

* * * * *